United States Patent [19]

Bergelson et al.

[11] Patent Number: 4,938,229

[45] Date of Patent: Jul. 3, 1990

[54] METHOD AND APPARATUS FOR TRANSMITTING DATA DESCRIPTIVE OF ELECTROMAGNETIC WAVEFORM

[75] Inventors: Michael N. Bergelson, Riverdale, N.Y.; Victor Parsonnet, Millburn, N.J.; Tim Daily, Philadelphia, Pa.

[73] Assignee: Paceart Inc., Wayne, N.J.

[21] Appl. No.: 187,945

[22] Filed: Apr. 29, 1988

[51] Int. Cl.⁵ ............................................. A61B 5/0402
[52] U.S. Cl. .................................... 128/696; 128/706
[58] Field of Search ............... 128/696, 706, 902, 903, 128/904; 455/302, 305

[56] References Cited

U.S. PATENT DOCUMENTS

| | | | |
|---|---|---|---|
| 3,717,857 | 2/1973 | Evans | 128/903 |
| 3,898,984 | 8/1975 | Mandel et al. | 128/696 |
| 4,053,932 | 10/1977 | Yamaguti et al. | 455/305 |
| 4,135,159 | 1/1979 | Kubanoff | 455/305 |
| 4,319,241 | 3/1982 | Mount | 128/904 |
| 4,409,984 | 10/1983 | Dick | 128/696 |
| 4,561,113 | 12/1985 | Naito | 455/305 |

Primary Examiner—Lee S. Cohen
Assistant Examiner—Scott Getzow
Attorney, Agent, or Firm—Howard C. Miskin

[57] ABSTRACT

A method and apparatus for transmitting data descriptive of an electromagnetic waveform wherein a constant amplitude signal is frequency modulated and transmitted to a remote site where digital signals are generated in response to zero crossings of the fm analog signal. Interrupt signals are generated in response to zero crossings for storing time differences between successive digital signals corresponding to the zero crossing which are then averaged at the Nyquist sampling rate to display and analyze a constructed waveform simulating the original signal.

11 Claims, 2 Drawing Sheets

METHOD AND APPARATUS FOR TRANSMITTING DATA DESCRIPTIVE OF ELECTROMAGNETIC WAVEFORM

BACKGROUND OF THE INVENTION

This invention provides a method and apparatus for transmitting and receiving data derived from an electromagnetic waveform and for analyzing and displaying the information. More specifically, the invention relates to the encoding, transmission, reception and decoding of information to recover the parameters of an electromagnetic waveform, i.e., one representing an electrocardiogram, in real time.

It is known in the art to transmit data derived from electronic waveforms such as from the electrocardiogram of a medical patient from a remote location in which the patient is situated to a central station where a physician is resident. Such apparatus is employed by paramedics who can transmit the electrocardiogram of a patient in distress to a physician at a central station, thereby enabling a single phYsician to monitor a relatively large geographic area through the use of paramedic personnel who need only be trained to apply an ECG measuring apparatus to the patient.

It is further known in the art to encode a continuous signal of varying amplitude into a continuous constant amplitude signal having a frequency which varies in proportion to the amplitude of the original signal. Frequence modulation, as this technique is known, is widely used in communications transmissions over the air or telephone lines. It is further known to recapture the information encoded on a frequency modulated constant amplitude continuous, e.g., sinusoidal, signal by demodulating the fm signal. For example, analog signal frequency modulationdemodulation is performed routinely in the transmission and reception of radio and television broadcast programming.

Analog fm demodulators are complex and prone to errors caused by analog component parameter drift and the introduction of delays due to inertial characteristics of necessary filters employed in analog circuitry.

The present invention overcomes the limitations of the prior art in providing for a method which can be economically implemented in apparatus to allow for interpretation of an fm signal by converting it to digital form, processing it, and reconstructing informational characteristics of the analog signal used to modulate the fm signal, in real time on a constructed simulation of the original signal through the use of standard circuitry readily found in a personal digital computer which can be configured according to the invention and operated and maintained with minimal training and expense.

SUMMARY OF THE INVENTION

The present invention includes a method and apparatus for deriving information from an electromagnetic waveform transmitted from a remote location including an fm modulator for detecting the amplitude of a continuous electromagnetic waveform of varying amplitude and modulating the frequency of a constant amplitude continuous carrier signal, a transmitter for transmitting the fm constant amplitude signal to a remote receiver, a detector for detecting threshold crossings of the continuous fm constant amplitude signal and producing digital signals in response thereto, processing means for comparing successive times of threshold crossings and determining their differences, averaging means for averaging consecutive differences, a memory for storing the averages and a display and recorder for reproducing a simulation of the original waveform and its parameters in real time for viewing and analysis.

It is therefore an object of the invention to provide a method and apparatus for receiving information descriptive of an electromagnetic waveform which is transmitted from a remote location.

Another object of the invention is to provide an apparatus and method for receiving data descriptive of an electromagnetic waveform transmitted from a remote location for real time processing and display.

A further object of the invention is to reproduce an amplitude modulated signal in the frequency domain which can be readily converted to digital form for processing and then to analog form for display.

Still a further object of the invention is to provide a method and apparatus for deriving information from an electromagnetic waveform transmitted from a remote location which can be achieved economically by implementation on a standard personal computer with minimal supporting apparatus.

Other and further objects of the invention will be apparent from the drawings and following description of a preferred embodiment of the invention in which like reference numerals are used to designate like parts in the various views.

DESCRIPTION OF THE PREFERRED EMBODIMENT

Figure 1:
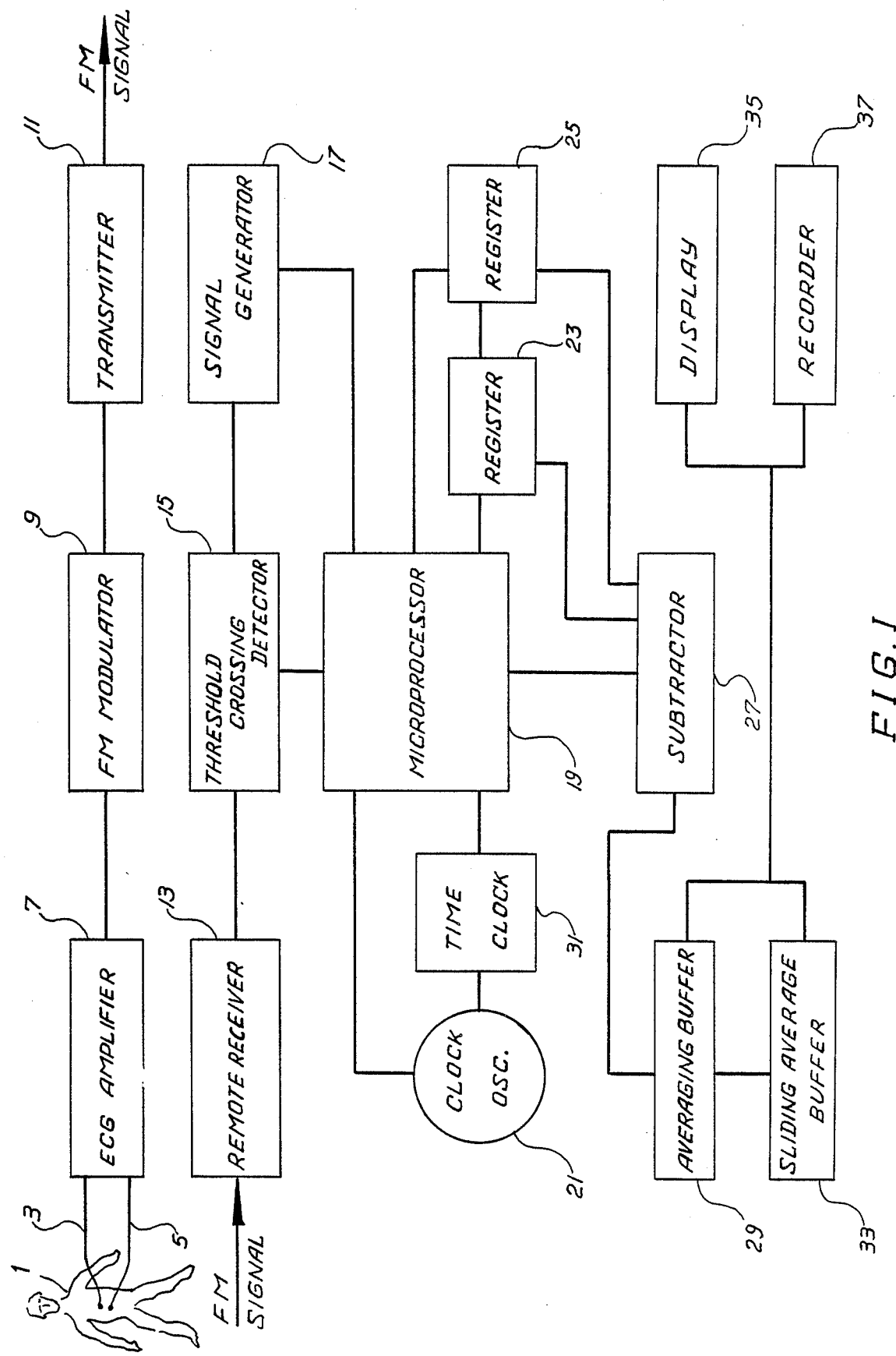
FIG. 1 is a schematic block diagram of the apparatus used to implement the method of the invention.
Figure 2A:
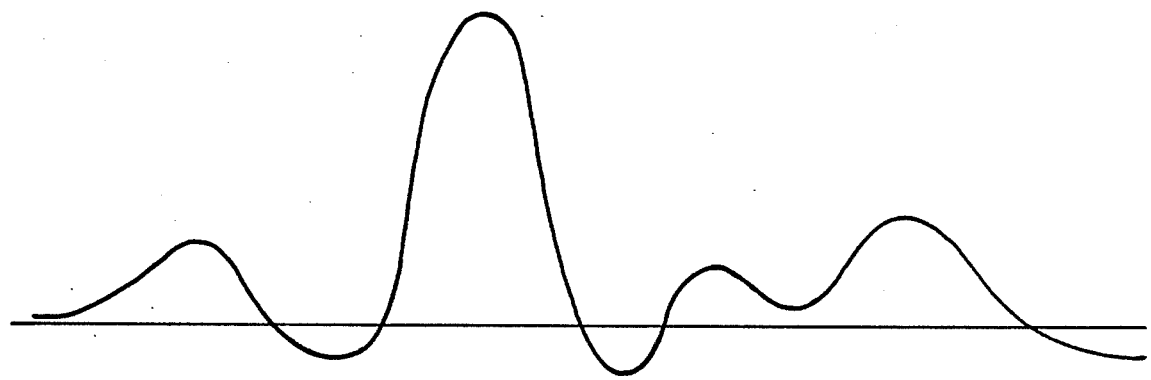
FIG. 2 (a) is a time versus amplitude plot of an electromagnetic waveform which is to be transmitted, analyzed and displayed according to the method and apparatus of the preferred embodiment of the invention.
FIG. 2(b) is a time versus amplitude plot of a constant amplitude waveform which is frequency modulated in accordance with the amplitude of the waveform of FIG. 2(a).
FIG. 2(c) is a time versus amplitude plot of digital signals generated in response to a threshold crossing of the waveform of FIG. 2(b).
Figure 2B:
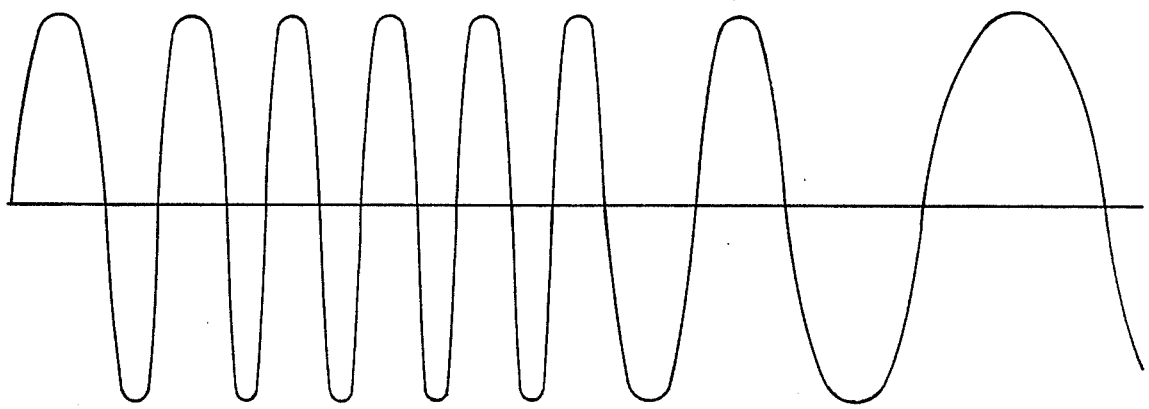

Referring now to FIG. 1 of the drawings, there is shown a patient 1 to whom electrodes 3 and 5 are affixed to record an electrocardiogram (ECG) waveform. The ECG sensed by the electrodes is applied to the input of an ECG amplifier 7, the output of which is a standard ECG waveform, which is amplified for further processing. The amplified output of the ECG amplifier 7, an example of which is shown in FIG. 2(a), is applied to the input of a fm modulator 9 wherein a constant amplitude sinusoidal electromagnetic waveform signal is produced with a frequency that varies in proportion to the amplitude of the output signal of the ECG amplifier 7, as shown in FIG. 2(b). The fm signal output of the modulator 9 is then applied to the input of a transmitter 11 which can be a telephonic transmitter or a radio frequency one for transmitting the constant amplitude frequency modulated sinusoidal signal to a remote receiver. Commercial transmitters of the foregoing type are sold under various trade names including Medtronic, Instromedix and Cordis. The baseline frequencies of the carrier signals, that is the frequency which is equivalent to zero amplitude of the input signal to be frequency modulated, may vary from the transmitter of one manufacturer to another. Where communication is by telephone, the baseline frequency is kept within the useful transmission frequency range of the telephone line band, which is about 2,000 hertz. For example, a Medtronic transmitter has been found to have a baseline frequency, corresponding to zero amplitude, of 1,450 hertz while a transmitter sold by Instromedix uses a 1,930 hertz baseline frequency for its carrier signals.

Figure 2C:

The fm signal output of the transmitter 11 is received at a remote receiver 13 which can be a telephone receiver connected to telephone lines or a radio frequency receiver, depending upon the type of transmitter 11 that is used. The output of the receiver 13 is connected to a threshold crossing detector 15 which generates a digital output signal pulse, as shown in FIG. 2(c), in response to each threshold crossing of the frequency modulated analog output signal of the receiver 13. In the preferred embodiment of the invention, the threshold at which the crossing is measured is zero volts and the threshold crossing detector 15 is a zero crossing detector.

The output of the zero crossing detector 15 is connected to an interrupt signal generator 17 which is connected to one of the interrupt lines of a microprocessor 19. A clock oscillator 21 provides timing signals to the microprocessor 19 which is connected to two event storage memories 23 and 25. Each time an interrupt signal is generated by the interrupt generator 17 in response to a zero crossing of the received signal as indicated by the output of the zero crossing detector 15, the microprocessor causes the time of the zero crossing to be stored in register 23 and the previous time stored in register 23 to be shifted to register 25. Hence after steady state operation is reached there are always stored in register 23 and register 25 the times of the most recent and immediately previous occurrences of the zero crossing of the received fm signal.

A digital subtractor 27 is connected to registers 23 and 25. In response to the generation of each interrupt signal from the interrupt generator 17, subtractor 27 subtracts the value of the time stored in register 25 from the value of the time stored in register 23 to compute the difference in time between the occurrences of the most recent and previous zero crossings of the input waveform. The calculated difference is stored in an averaging buffer 29 which can comprise one or more connected reentrant shift registers for storing a sequence of numbers corresponding to consecutive time differences between zero crossings of the input waveform.

The adverse affects of spurious signals and other artifacts are avoided by testing the times between each pair of successful interrupt signals from the interrupt signal generator 17 in the microprocessor to ascertain if they are within the bandwidth corresponding to the frequencies which represent the amplitude of an electrocardiogram waveform. When the measured difference between the time stored in registers 23 and 25 is not within the allowable bandwidth, an artifact flag is set to discount the erroneous value. In addition, the use of an average calculated over a series of successive time differences between interrupt signals stored in the averaging buffer 29 lessens the influence of any single erroneous time difference.

The averaging buffer 29 separately accumulates and stores the last K values of the time differences between successive zero crossings as indicated by interrupt signals from the interrupt generator 17, where K is an integer that can be selected depending on the speed of desired system response. In the preferred embodiment of the invention, K is in the range of 2 to 4. As each new time difference enters the averaging buffer 29, the previous values are shifted and the earliest one is lost.

A real time clock 31 including a frequency divider receives high frequency signals from the system clock oscillator 21 and generates clock signals at a lower frequency which are applied to another interrupt line of the microprocessor 19. The resulting interrupt signal output of the real time clock 31 causes K values of the time differences stored in the averaging buffer 29 to be transferred to the CPU 19 for determining their average by summing the K differences and dividing the sum by K. The computed average of the time differences is inversely proportional to a corresponding amplitude of the transmitted analog signal and can therefore be used to construct a simulated signal for analysis and display.

Signals are generated by the real time clock 31 at a frequency no less than the Nyquist frequency which is equal to twice the frequency of the ECG signal which is to be constructed.

Assuming a nominal frequency of the ECG signal of 80 hertz, the Nyquist rule dictates that the signal generating frequency of the real time clock 31 be 160 hertz. Thus every 0.625 miliseconds the real time clock 31 generates an interrupt signal which causes the CPU 19 to accept the last K time difference values stored in the averaging buffer 29 for averaging as heretofore explained.

A sliding average buffer 33 is also provided for storing the N most recent averages. The interrupt signal generated by the real time clock 31 also causes the CPU 19 to accept the last N time difference values stored in the sliding buffer 33 for determining a long term average. In the preferred embodiment of the invention, $N=4$.

The short and long term averages derived from the data stored in the buffers 29 and 33 can then be graphically displayed on an electronic cathode ray tube display 35 or plotted on a chart recorder 37. The apparatus of the invention utilizes concurrency of processing whereby averaging of the time differences and display of the various waveforms takes place in between interrupt signals from the real time clock 31. The foregoing method can be accomplished on apparatus including a zero crossing detection circuit known in the art and a conventional personal computer which can be programmed to execute the methods steps described herein as will be known to a skilled programmer given knowledge of the disclosure herein set forth.

It is to be appreciated that variations and modifications can be made to the preferred embodiment described herein without departing from the spirit and scope of the invention which is to limited only by the following claims.

What is claimed is:

1. An apparatus for deriving information from a remotely situated electromagnetic waveform having a characteristic with a time varying magnitude comprising:
   fm modulator means for detecting the varying magnitude of said electromagnetic waveform and modulating the frequency of a constant amplitude continuous carrier signal in response thereto;
   transmitter means operatively connected to said fm modulator means for transmitting the fm constant amplitude signal to a remote location;

detector means operatively connected to a receiver for detecting threshold crossings of the continuous fm constant amplitude signal;

subtractor means operatively connected to said detector means for comparing successive times of said threshold crossings and determining their differences; and signal generator means operatively connected to said subtractor means for constructing a signal having a characteristic with a time varying magnitude corresponding to said characteristic with time varying magnitude of said remotely situated electromagnetic waveform.

2. Apparatus according to claim 1 wherein said signal generator means further comprises first buffer means for storing a plurality of the differences determined by said subtractor means and a processor means for determining the average of said plurality of differences, said signal generator means being responsive to said average of said plurality of differences.

3. Apparatus according to claim 2 wherein said signal generator means comprises second buffer means for storing a plurality of first averages and processor means for determining the average of said first averages, said signal generator means being further responsive to said average of said first averages.

4. Apparatus according to claim 2 or 3 further comprising interrupt signal generator means operatively connected to said detector means for periodically generating interrupt signals, said processor means being responsive to said interrupt signals for concurrent processing by determining an average of the time differences of said threshold crossings between said interrupt signals.

5. Apparatus for deriving information from a frequency modulated waveform comprising detector means having an input to which said waveform can be applied for detecting threshold crossings thereof, subtractor means operatively connected to said detector means for comparing successive times of said threshold crossings and determining their differences, and signal generator means operatively connected to said subtractor means for constructing a signal having a characteristic with a time varying magnitude corresponding to said determined time differences.

6. Apparatus according to claim 5 further comprising display means operatively connected to said signal generator means for presenting a graphic reproduction of said constructed signal.

7. Apparatus according to claim 6 wherein said display means comprises a cathode ray tube.

8. Apparatus according to claim 6 wherein said display means comprises a chart recorder.

9. A method for deriving information from a remotely situated electromagnetic waveform having a characteristic with a varying magnitude comprising detecting the varying magnitude of said electromagnetic waveform and modulating the frequency of a constant amplitude continuous carrier signal in response thereto, transmitting the fm constant amplitude signal to a remote location, receiving the fm constant amplitude signal at said remote location, detecting threshold crossings of the continuous fm constant amplitude signal received at said remote location, comparing successive times of said threshold crossings, determining the differences between said successive times of said threshold crossings, and constructing a signal having a characteristic with a time varying magnitude corresponding to said differences between said successive times of said threshold crossings.

10. A method according to claim 9 further comprising averaging K successive differences of the times of said threshold crossings and constructing a signal having a characteristic with a time varying magnitude corresponding to said average where K is an integer.

11. A method according to claim 10 further comprising averaging N successive averages of said threshold crossings and constructing a signal having a characteristic with a time varying magnitude corresponding to said average of averages where N is an integer.

* * * * *